US012010458B2

(12) United States Patent
Schoenberg

(10) Patent No.: US 12,010,458 B2
(45) Date of Patent: *Jun. 11, 2024

(54) SINGLE POINT DEVICES THAT CONNECT TO A DISPLAY DEVICE

(71) Applicant: American Well Corporation, Boston, MA (US)

(72) Inventor: Roy Schoenberg, Boston, MA (US)

(73) Assignee: American Well Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/110,683

(22) Filed: Feb. 16, 2023

(65) Prior Publication Data

US 2023/0276024 A1 Aug. 31, 2023

Related U.S. Application Data

(63) Continuation of application No. 17/063,156, filed on Oct. 5, 2020, now Pat. No. 11,589,003, which is a
(Continued)

(51) Int. Cl.
*H04N 7/14* (2006.01)
*G16H 80/00* (2018.01)
*H04L 65/1069* (2022.01)
*H04L 65/403* (2022.01)
*H04L 65/60* (2022.01)
*H04N 7/15* (2006.01)
*H04N 21/2187* (2011.01)
*H04N 21/422* (2011.01)
(Continued)

(52) U.S. Cl.
CPC ............. *H04N 7/147* (2013.01); *G16H 80/00* (2018.01); *H04L 65/1069* (2013.01); *H04L 65/403* (2013.01); *H04L 65/60* (2013.01); *H04N 7/142* (2013.01); *H04N 7/15* (2013.01); *H04N 21/2187* (2013.01); *H04N 21/42204* (2013.01); *H04N 21/4316* (2013.01); *H04N 21/47* (2013.01)

(58) Field of Classification Search
CPC ....... H04N 31/42201; H04N 21/42203; H04N 7/142; H04N 7/15; H04N 21/4316; H04N 7/147; H04N 21/47; G16H 80/00; H04L 65/1059; H04L 65/80; H04L 65/4015; H04L 65/1069; H04L 65/403
USPC ........................................... 348/14.01–14.16
See application file for complete search history.

(56) References Cited

U.S. PATENT DOCUMENTS 7,590,550 B2   9/2009  Schoenberg
7,835,926 B1 *  11/2010 Naidoo ................... G16Z 99/00
                                              705/2
(Continued)

FOREIGN PATENT DOCUMENTS

WO    WO 2019/035007    2/2019

*Primary Examiner* — Quoc D Tran
(74) *Attorney, Agent, or Firm* — Fish & Richardson P.C.

(57) ABSTRACT

Single point devices that connect to a display device include a port for establishing a connection to a port on the display device and for switching the display device from a first mode to a second mode; an audio video device configured to capture image data representing one or more images of physical entities in a field of view of the audio video device and further configured to capture acoustic data; a receiver device and a transmitter device configured for dedicated communication with a data processing system.

15 Claims, 12 Drawing Sheets

Related U.S. Application Data continuation of application No. 16/547,243, filed on Aug. 21, 2019, now Pat. No. 10,798,338.

(51) Int. Cl.
*H04N 21/431* (2011.01)
*H04N 21/47* (2011.01)

(56) References Cited

U.S. PATENT DOCUMENTS

| | | |
|---|---|---|
| 10,798,338 B1 | 10/2020 | Schoenberg |
| 11,589,003 B2 | 2/2023 | Schoenberg |
| 2003/0041333 A1 | 2/2003 | Allen et al. |
| 2004/0019503 A1* | 1/2004 | Berenguer ............... H04N 7/18 705/2 |
| 2007/0291736 A1 | 12/2007 | Furlong et al. |
| 2011/0214153 A1 | 9/2011 | Rosenfeld |
| 2014/0253665 A1 | 9/2014 | Nietfeld et al. |
| 2015/0238150 A1 | 8/2015 | Subramaniam |
| 2016/0088257 A1 | 3/2016 | Kim et al. |
| 2016/0183796 A1 | 6/2016 | Fukuma et al. |
| 2017/0032092 A1 | 2/2017 | Mink et al. |
| 2017/0039338 A1 | 2/2017 | Khindaria et al. |
| 2019/0096534 A1 | 3/2019 | Joao |
| 2019/0221097 A1* | 7/2019 | Saneii ................... H04N 7/147 |
| 2019/0318825 A1 | 10/2019 | Shaw |
| 2021/0266499 A1 | 8/2021 | Schoenberg |

* cited by examiner

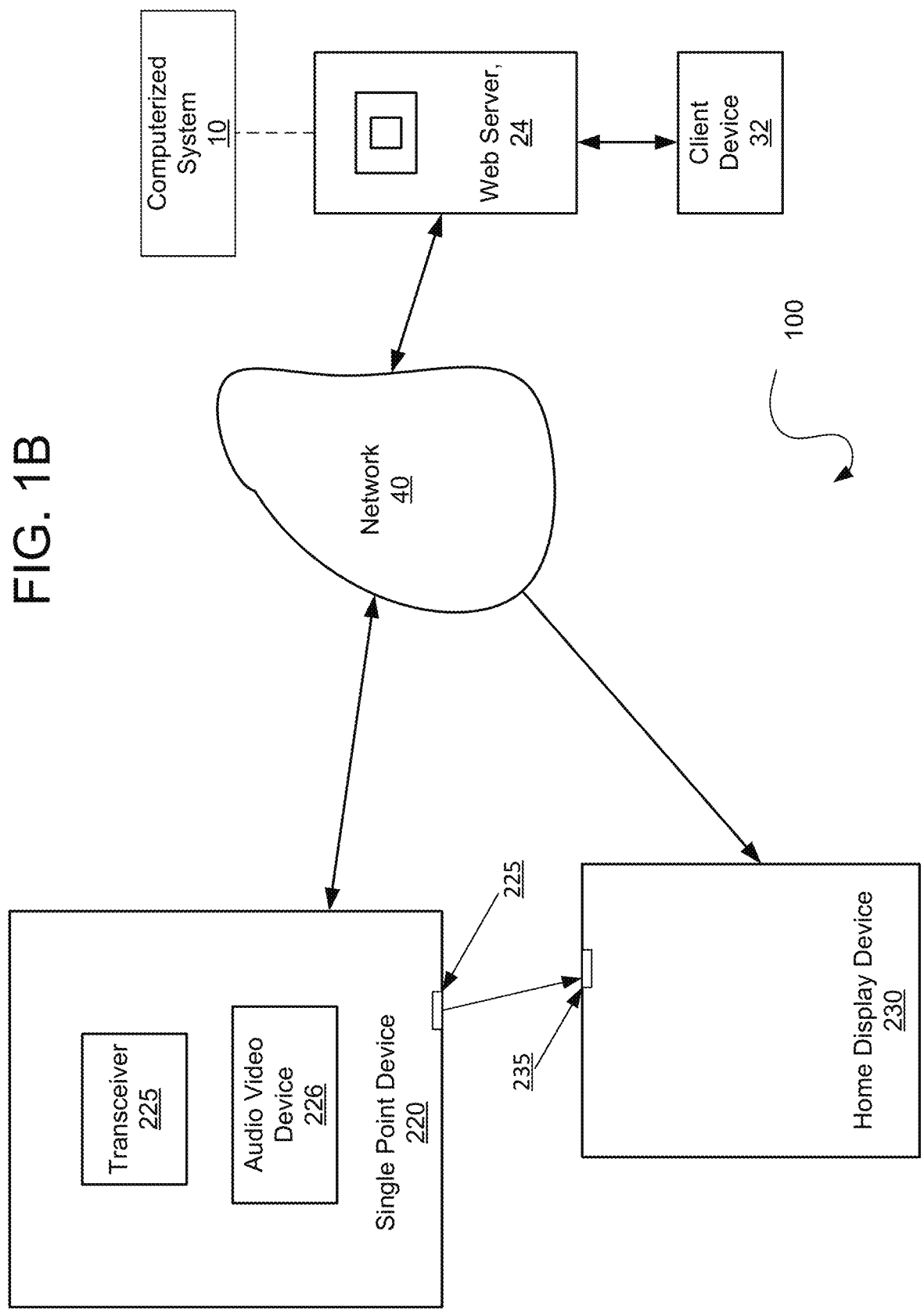

SINGLE POINT DEVICES THAT CONNECT TO A DISPLAY DEVICE

RELATED APPLICATIONS

This application is a continuation and claims priority under 35 U.S.C. § 120 to U.S. application Ser. No. 17/063,156, filed on Oct. 5, 2020, which is a continuation and claims priority under 35 U.S.C. § 120 to U.S. application Ser. No. 16/547,243, filed on Aug. 21, 2019, (U.S. Pat. No. 10,798,338) the entire contents of each of which are hereby incorporated by reference.

BACKGROUND

The present disclosure is directed to connecting consumers with service providers using a single point device.

Systems have been developed to connect consumers and their providers over the Internet and the World Wide Web. Some systems use e-mail messaging and web-based forms to increase the level of connectivity between a member of a health plan and his assigned health care provider. The consumer sends an e-mail or goes to a website that generates and sends a message (typically an e-mail or an e-mail type message) to a local provider. These types of services have been broadly referred to as "e-visits." While generally viewed as an addition to the spectrum of services that may be desired by consumers, the benefits of such services are not clear. One of the concerns associated with offering additional communication channels, such as e-mail, is that it can result in over consumption of services, rather than provide for better coordination.

Plans are embracing the notion of consumerism by offering advanced tools for consumers to become informed and acquire medical services. Facilitating timely and more organized communication between the member and their provider is perceived as a natural investment in the new consumer-driven healthcare world. While still at an early stage, interest in e-visits has picked up both in the commercial world as well as in the strategic planning sessions of health plans around the country. Vendors offering health portals for health plans typically now describe their roadmap for the incorporation (or interfacing with) e-visit platforms. An example of an e-visit platform is described in U.S. Pat. No. 7,590,550, the entire contents of which are incorporated herein by reference.

SUMMARY

In an aspect, a single point device is provided. The single point device includes a port for establishing a connection to a port on a display device and for switching the display device from a first mode to a second mode, wherein the display device is configured to render a program in the first mode and is further configured to stream data for a communication session received from a data processing system in the second mode, wherein the data processing system configured to receive requests from medical service providers to initiate live time communication sessions with a user of the display device. The single point device includes an audio video device configured to capture image data representing one or more images of physical entities in a field of view of the audio video device and further configured to capture acoustic data. The single point device includes a receiver device. The receiver device is configured for dedicated communication with a data processing system that receives requests from medical service providers to initiate live time communication sessions with a user of the display device. The receiver device is configured to receive (a) audio signals, during a live time communication session, from a client device of an identified medical service provider through the data processing system, and (b) a user interface signal from the data processing system and carrying user interface data that is renderable on the display device that, when rendered by the display device, causes the display device to interrupt a program displaying on the display device. The single point device includes a transmitter device. The transmitter device is configured for dedicated communication with the data processing system that receives a request from a medical service provider to initiate a live time communication sessions. The transmitter device is configured to transmit, through the data processing system and to the client device, image data captured by the audio video device and audio signals received from the audio video device. The transmitter device is configured to transmit the user interface signal received from the receiver device to the display device in the second mode to cause the display device to interrupt the program to initiate the communication session, as requested by the medical service provider.

The receiver device can be further configured to receive a user interface signal to render a graphical user interface to prompt the user of the display device for authorization to establish a communication session through the data processing system with the client device of the identified medical service provider. The audio video device can include a microphone. The audio video device can include a speaker device configured to output the audio signals received by the receiver device. The audio video device can include a camera.

The display device can include a television display. Causing the display device to interrupt the program and render the graphical user interface can include causing the display device to cease displaying of the program. Causing the display device to interrupt the program and render a graphical user interface can include causing the display device to display the graphical user interface in a first portion of the display device and continue displaying the program in a second portion of the display device. The first portion can be larger than the second portion.

The dedicated communication with the data processing system can be established through a wireless network. The receiver device can be further configured to receive, from a control device, control signals indicating that the user has authorized interruption of the program.

In an aspect, a method implemented by a data processing system for rendering live streamed data responsive to provider initiated requests for consultations is provided. The method includes receiving, from a client device of a medical service provider, a request to initiate a communication with a client device of a patient. The method includes, responsive to the request to initiate the communication, transmitting, by the data processing system to a single point device that is communicatively coupled to a display device, a signal that causes the display device to switch input modes from a first mode to a second mode, with the first mode being a mode for rendering a program and with the second mode being a mode for streaming data received from the data processing system. The method includes transmitting, to the single point device, a user interface signal carrying graphical user interface data that when rendered by the display device in the second mode interrupts displaying of a program on the display device and renders a graphical user interface, with the graphical user interface prompting a viewer of the display device for updates on a health status of the viewer and initiating a communication session. The method includes establishing, by the data processing system, the communication session between the single point device and the client device.

The method can further include causing the graphical user interface to update with a prompt for authorization to establish a communication session through the data processing system with a client device of a medical service provider. The method can further include receiving, by the data processing system from the single point device, authorization data instructing the data processing system to establish the communication session. The method can further include detecting, by the data processing system, completion of the communication session. The method can further include, responsive to the detecting, sending termination data to the single point device that, when received by the single point device, causes the single point device to cease rendering the graphical user interface on the display device and causing the display device to return to displaying the program. The method can further include tracking the availability of a plurality of service providers. The method can further include receiving, based on the tracking, an indication that one or more service providers of the plurality of service providers are available for establishing a communication session.

The one or more service providers can include two or more service providers. Before transmitting the graphical user interface to the single point device, the method can further include selecting one of the two or more service providers for establishing the communication session.

Selecting one of the two or more service providers can be based on health data of a user received from the single point device. The communication session can be a full duplex communication session. The communication session can be a videoconference communication session.

Interrupting the displaying of the program can include causing the display device to display the graphical user interface in a first portion of the display device and continue displaying the program in a second portion of the display device. The first portion can larger than the second portion. Interrupting the displaying of the program can include causing the display device to cease displaying of the program.

These and other aspects, features, and implementations can be expressed as methods, apparatus, systems, components, program products, methods of doing business, means or steps for performing a function, and in other ways, and will become apparent from the following descriptions, including the claims.

BRIEF DESCRIPTION OF THE FIGURES

FIGS. 1A-1B are block diagrams depicting environments including a single point device connected to a home display device and a computerized system executing on a web server.

DETAILED DESCRIPTION

Overview

Figure 1A:
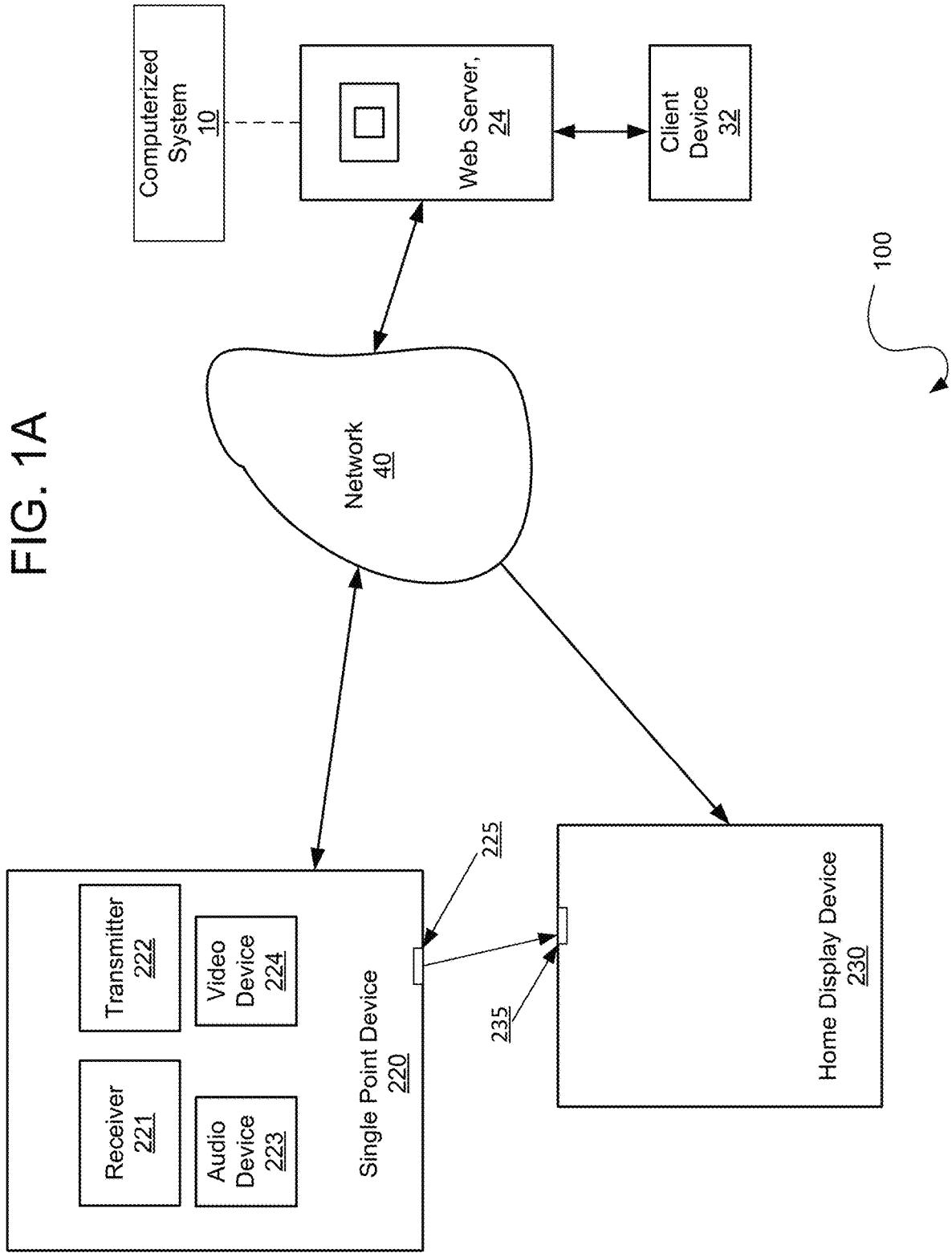

Described herein is a single point device (e.g., a voice interactive system) that can control and invoke a telehealth ecosystem and can provide for a telehealth consult through a home display device (for example, a television device). The single point device is configurable to be placed on top of a home display device (such as a television display) and connect through an audio and video interface port on the home display device (for example, a high-definition multimedia interface port) to enable consumers (for example, medical patients) to interact with physicians and other service providers through the single point device (and using the home display device). In some implementations, the single point device is registered through a server that has the ability to link to the computerized system functionality to "beam" a doctor into the room of the patient for a telehealth consult.

The single point device includes video and audio functionality to enable real-time video conferencing. As described later in further detail, the single point device can operate in one or more functionalities, including surveillance mode, help mode, or scheduled visit mode. The single point device communicates with an integrated information and communication platform to permit providers to initiate consults and points of contacts with consumers. In an alternate embodiment, consumers of services identify and prioritize service providers with whom they should consult and to carry out consultations with such service providers in an efficient manner. The computerized system described in this specification integrates the described single point device such that the platform can provide initiation—by providers of consults, surveillance, help and scheduling services to consumers. The single point device (or virtual assistant device) can be used for a visiting nurse visit, a scheduled visit, a family visit, urgent care and so forth.

Described herein is a system that enables a provider to initiate a consultation with a patient at a time that the provider wants to do so. In this system, the directionality of communication is with the provider initiating the communication, e.g., because the provider wants to "virtually" walk in to a patient's rooms and check-up on or perform surveillance on the patients. In some examples, this provides a form of access control, where the provide controls when the providers gains access to the patient.

In an example, the patient is watching television. Connected to the television is a single point device that is communicates with a dedicated surveillance or communication system, e.g., a brokerage system. At any or various points in time, e.g., as the patient is watching TV, the service provider (e.g., doctor) may interrupt the program and initiate a communication with the patient, inquiring how the patient is doing. If the single point device is paired or otherwise connected to other external devices (e.g., electronic medical record systems), the single point device may transmit data directly to the other devices.

In some example, the provider decides to initiate a communication with the patient when the service provider knows that the patient is in front of the TV screen or in proximity to the TV screen. Many techniques may be used to detect when the patient is in a field of a view of the single point device, including, e.g., face detection/face tracking, electronic pan/tilt zoom of a video camera that is part of the single point device, detection of ambient noise or a lack thereof, light manipulation devices, and so forth.

In another example, rather than the service provider initiating the request, the single point device is configured to listen to inbound requests (in listening mode). For example, a patient may request a consultation by speaking to the single point device. In this example, the single point device may have wake on sound technology where the device is listening for a key word, e.g., a name of the device, which causes the device to "wake up" and shift into a higher power mode for performing voice detection and establishing a communication session.

In some examples, the single point device is connected to home biometric devices (e.g., a blood pressure cuff, remote monitoring device, home examination devices, and so forth) to facilitate collection of biometric data.

In some examples, the single point device includes patient motion detection devices, e.g., to detect when a patient falls, which would then allow a physician to initiate a consultation or otherwise drive the consultation. In these circumstances, the patient is passive and the single point device is used for access control. The single point device is also configured to control volume and switch input modes of the display device, e.g., the TV. The single point device may also include beam forming microphones.

FIG. 1A is a block diagram depicting an environment 100 including a single point device 220 communicatively coupled to a home display device 230 and an engagement computerized system 10 executing on a web server 24. The single point device 220 includes an audio device 223, a video device 224, a receiver 221, a transmitter 222 and an interface port 225. The audio device 223 includes one or more transducers, such as microphones, configured to capture acoustic data and convert the acoustic data into an electrical signal (or optical signal). In some implementations, the audio device 223 includes one or more electroacoustic transducers, such as loudspeakers, that convert electrical signals (or optical signals) into audible sound. Implementations in which the audio device 223 includes one or more electroacoustic transducers (for example, loud speakers) can be particularly useful when the display device 230 does not include integrated speakers itself. The video device 224 includes an imaging device, such as a camera, that can capture raw image data. The video device 224 can also include digital signal processing for processing the captured raw image data. The receiver 221 is configured to receive signals and the transmitter 222 is configured to transmit signals. In some implementations, the receiver 221 and the transmitter 222 are integrated into a single transceiver.

In some implementations, the single point device 220 includes voice interaction facilities that wake-up to activate the device 220 using a wake-word (such as "help," "schedule," or "surveil"). In some implementations, a user can say the word "help", and the audio device 223 can capture the user's words and the captured words can be used to wake-up the single point device 220. In some implementations, the single point device 220 is configured to be communicatively coupled to a virtual assistant device which can activate the single point device 220 using a wake-up word, as described later with reference to FIG. 4. The single point device 220 includes function controls to connect to a computerized system 10 executing on the web server 24. The single point device 220 can have built in support to connect directly to the computerized system to supply customer account information. The single point device 220 responds to commands and establishes communication channels between a customer and a provider through the computerized system 10. There are a number of means for sending messages (that is, signals carrying data) from the single point device 220. In some implementations, the single point device 220 delivers messages to the computerized system 10. In some implementations, the single point device 220 is able to send messages such as video synchronized with audio. For households with more than one member, the single point device 220 can provide messaging support to anyone in the household.

The web server 24 can be a cloud-based service that provides APIs to interface with the single point device 220. The single point device 220 is configured to be communicatively coupled to the computerized system 10 (via the network 40 and web server 24).

The single point device 220 is configured to be communicatively coupled to a home display device 230 via either a one way or a two way communication channel. The single point device 220 is configured to be communicatively coupled to the home display device 230 via the interface port 225 of the single point device 220 and an interface port 226 of the home display device 230. The interface ports 225,235 can be one of several types of interface ports, such as HDMI ports, digital visual interface (DVI) ports, video graphics array (VGA) ports, and so forth. In some implementations, the home display device 230 is a television receiver. In some implementations, the home display device 230 includes either a one way or a two way communication channel connection to either Internet streaming services or cable services.

The transmitter 222 is configured for dedicated communication with the computerized system executing on the web server 24. In some implementations, the transmitter 222 is configured to establish a dedicated communication channel with the web server 22 through wireless communications using the network 40. The transmitter 222 is configured to transmit, through the computerized system 10, audio signals and video signals to a client device 32 of a service provider. The client device 32 can be substantially similar to the single point device 220. The audio signals can carry data corresponding to the acoustic data captured by the audio device 223 and the video signals can carry data corresponding to the image data captured by the video device 224. The receiver 221 is also configured for dedicated communication with the computerized system executing on the web server 24. In some implementations, the receiver 221 is configured to establish the same dedicated communication channel with the web server 22 as the transmitter 222. The receiver 221 is configured to receive audio signals and video signals, through the computerized system 10 and during a real-time communication session, from the client device 32 of a service provide. The receiver 221 is also configured to receive, from the computerized system 10, a user interface signal carrying user interface data.

The transmitter 222 can transmit the received user interface signal to the home display device 230 to cause the home display device 230 to render a user interface. The user interface data causes the home display device 230 to interrupt a program displaying on the home display device 230 (for example, a televised program, a streamed program, a digital versatile disk program, and so forth). In some implementations, the home display device 230 interrupts the program by ceasing the display of the program and, instead, displaying a user interface in accordance with the user interface data (see, for example, FIG. 5B). In this example, the patient is passive and is simply watching the television program. In this example, the provider interrupts to program to initiate the communication with the patient.

In some implementations, the home display device 230 interrupts the program by displaying the user interface in one portion of the home display device 230 while continuing the display of the program in a second portion of the home display device 230 (for example, using picture-in-picture). The user interface can prompt the user of the single point device 220 to authorize the establishing of a communication session (service session) though the computerized system 10. However, in other examples, authorization is not required and the single point device simply interrupts the program and establishes the communication with the service provider. In some implementations, the user of the single point device 220 can use a remote control device to send control signals to the single point device 220 (which are received by the receiver 221) to indicate authorization of the communication session (for example, by selecting a "yes" icon; see FIG. 5B). The single point device 220 can then send a signal to the computerized system 10 to indicate that the user has authorized the communication session, and the computerized system 10 can establish a communications session between the single point device 220 and the client device of the service provider.

While the implementation shown in FIG. 1A describes the audio device 223 and the video device 224 as separate devices, other implementations are not so limited. As shown in FIG. 1B, in some implementations, audio device 223 and video device 224 are integrated into a single audio video device 226. Any of the operations described in this specification with regard to the audio device 223 and/or video device 224 can be performed by the audio video device 226. While the implementation shown in FIG. 1A describes the receiver 221 and the transmitter 222 as separate devices, other implementations are not so limited. As shown in FIG. 1B, in some implementations the receiver 221 and the transmitter 222 are integrated into a single transceiver device 225. Any of the operations described in this specification with regard to the receiver 221 and/or transmitter 222 can be performed by the transceiver device 225.

Figure 2:
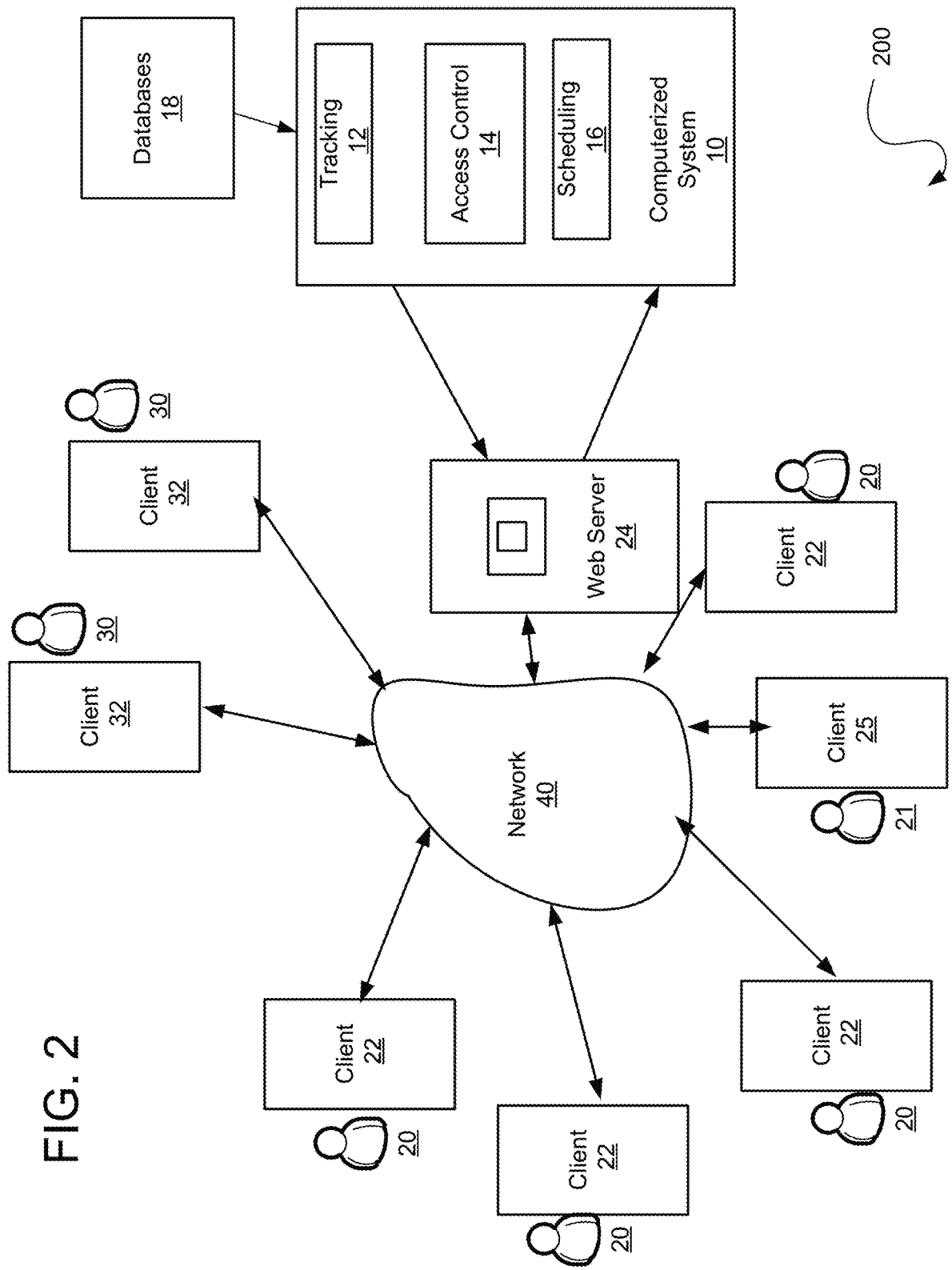
FIG. 2 is a block diagram depicting an environment in which a computerized system is operating.

FIG. 2 is a block diagram depicting an environment 200 in which a computerized system is operating. The environment 100 includes the computerized system 10 for making connections, over a network 40, between consumers 20, 21 at client systems 22, 25 and service providers 30 at client systems 32. Generally, the computerized system 10 is a data processing system configured to facilitate the rendering of live streamed data by implementing a brokerage service system. In some implementations, the network 40 includes the Internet or other types of networks. In some implementations, the computerized system 10 operates as a service running on a web server 24. In some implementations, one of more of the client systems 22, 25 include a single point device (such as the single point device 220 discussed earlier with reference to FIG. 1) that sends a message including a health status keyword(s) to the computerized system 10 and receives, from the computerized system 10, a connection request to an identified provider 30 based on the sent health status. The client systems 22, 25 can receive video and or audio data of a communication session with the service provider 30, and render the received video and or audio data of a communication session with the service provider on a home display device of the client systems 22, 25 of a consumer 20, 21. In some implementations, one or more client systems 22, include the single point device connected to a television receiver monitor (i.e., home display device) through high-definition multimedia interface (HDMI) port and, using a remote control device corresponding to the television receiver monitor, a consumer 20 can toggle through the home display device functionality or access the single point device.

The computerized system 10 includes an availability or presence tracking module 12 for tracking the availability of the service providers 30. Availability or presence can be tracked actively or passively. During active tracking, one or more of the service providers 30 provides an indication to the computerized system 10 that the one or more service providers 30 are available to be contacted by consumers 20, and an indication of the mode by which the provider may be contacted. The computerized system 10 includes a scheduling module 16, which locates providers 30 and establishes service session engagements, to enable a consumer 20, 21 to schedule a visit via the system 10 to engage such provider(s) 30 or to find other available providers 30, and to sequentially engage providers 30. The scheduled visit can be patient-initiated or provider-initiated. In some implementations, the computerized system 10 includes an access control facility 114, which manages and controls whether a given consumer 20 may access the system 10 and what level or scope of access to the features, functions, and services the system 10 will provide.

In some implementations, the provider's 30 computer, phone, or other terminal device periodically provides an indication of the provider's 30 availability (e.g., available, online, idle, busy) to the computerized system 10 and a mode (e.g., text, voice, video, etc.) by which the provider 30 can be engaged. In some implementations, the computerized system 10 presumes that the service provider 30 is available by the service provider's 30 actions, including connecting to the computerized system 10 or registering the provider's 30 local phone number with the computerized system 10. In some examples of a passive system, the computerized system 10 assumes the provider 30 is available at all times until the provider 30 logs off, except when the provider 30 is actively engaged with a consumer 20. The computerized system 10 accesses one or more databases 118 to retrieve data records with fields, the values of which specify the availability of various service providers. In an example, each data record is keyed, e.g., includes a field with a value that is a key that uniquely identifies a particular service provider. In this example, the computerized system 10 accesses the one or more databases 118 and searches the keyed data records for fields with values representing current availability for a consultation. The components of the computerized system 10 and the web server 24 may be integrated or distributed in various combinations as is commonly known in the art.

Figure 3:
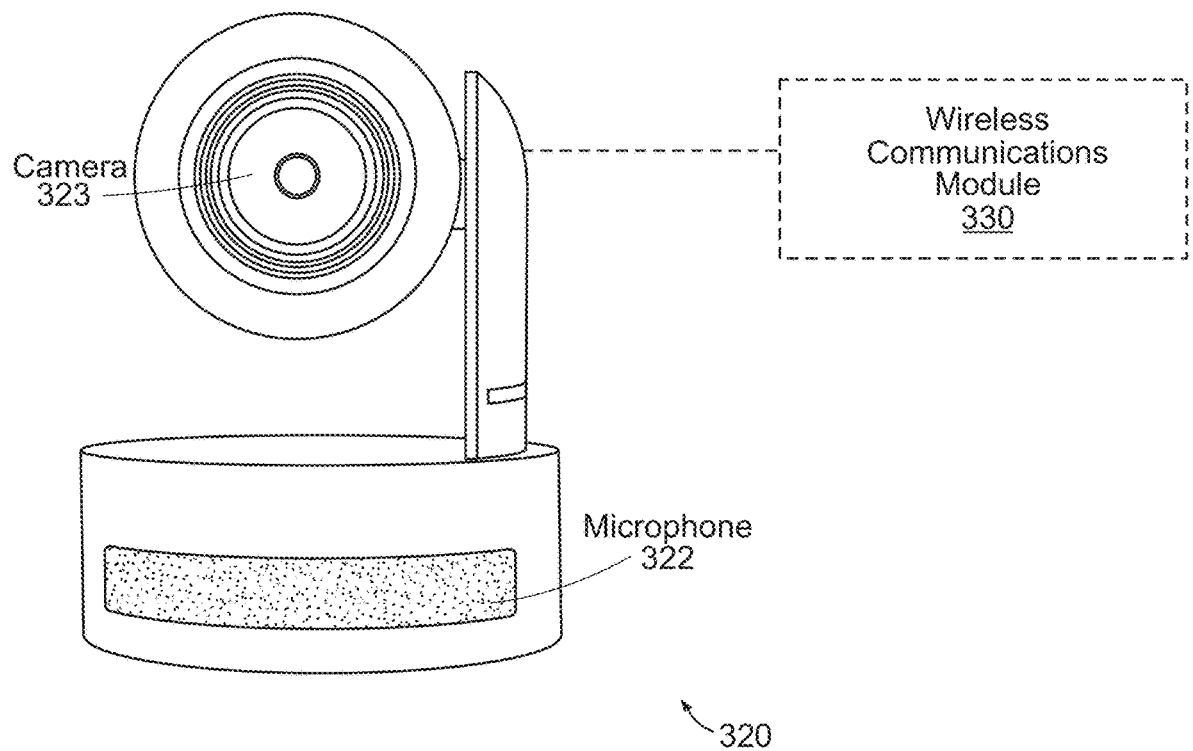
FIG. 3 shows one example of a single point device configured to be communicatively coupled to a home display device and a computerized system.

FIG. 3 shows one example of a single point device 320 configured to be communicatively coupled to a home display device and a computerized system. The single point device 320 can be the single point device 220 discussed previously with reference to FIG. 2. The single point device 320 includes a wireless communications module 330 (such as WiFi™) for connecting, via a wireless network, to the computerized system. The single point device 320 also includes a camera 323 for capturing optical information and a microphone 322 for capturing acoustic information.

Figure 4:
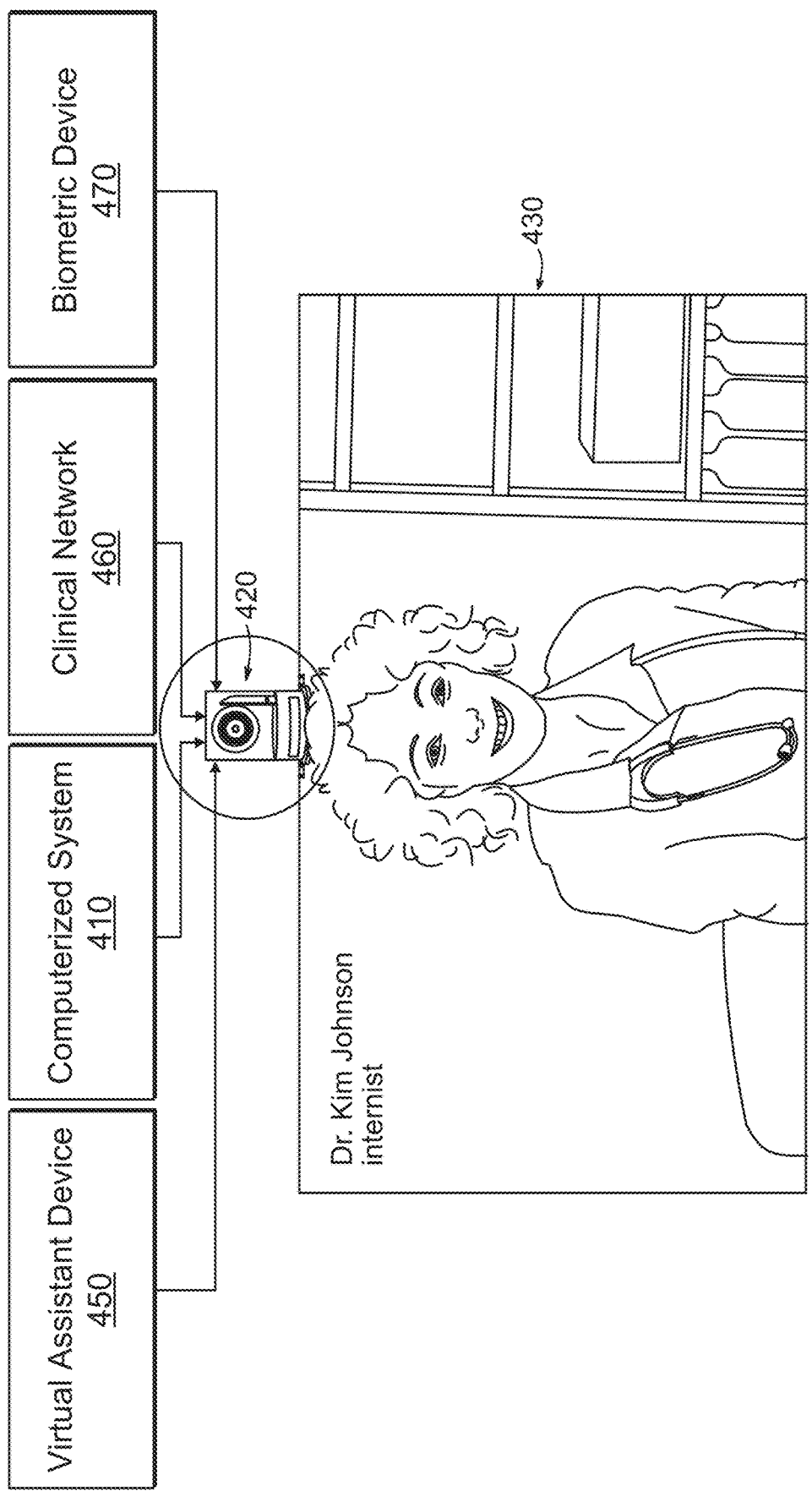
FIG. 4 illustrates a single point device integrating multiple data streams

FIG. 4 illustrates a single point device 420 integrating multiple data streams. The single point device 420 can be the single point device 220 discussed previously with reference to FIG. 1. The single point device 420 is capable of receiving activating data from a virtual assistant device 450. As discussed previously with reference to FIG. 1, the virtual assistant device 450 can cause the single point device 420 to activate upon detecting a wake-up word (such as "Help"). The single point device 420 is capable of receiving audio, video, and user interface data from the computerized system 410. The single point device 420 is capable of receiving data from a clinical network 460. In some implementations, the single point device 420 is configured to be communicatively coupled with a local network (for example, a local network of a hospital) and receiver audio, video, and user interface data from the clinical network 460. The single point device 420 is capable of receiving biometric data from one or more biometric devices 470. In some implementations, the single point device 420 is configured to be communicatively coupled with one or more heart monitors, one or more pulse monitors, and so forth. The biometric data can include blood pressure values, pulse values, and so forth. The single point device 420 can be configured to transmit this data through at least one of the clinical network 460 or the computerized system 410. The single point device 420 can present the data received from the computerized system 410, clinical network 460, and biometric devices 470 to a user using a home display device 430 that is communicatively coupled to the single point device 420.

Figure 5A:
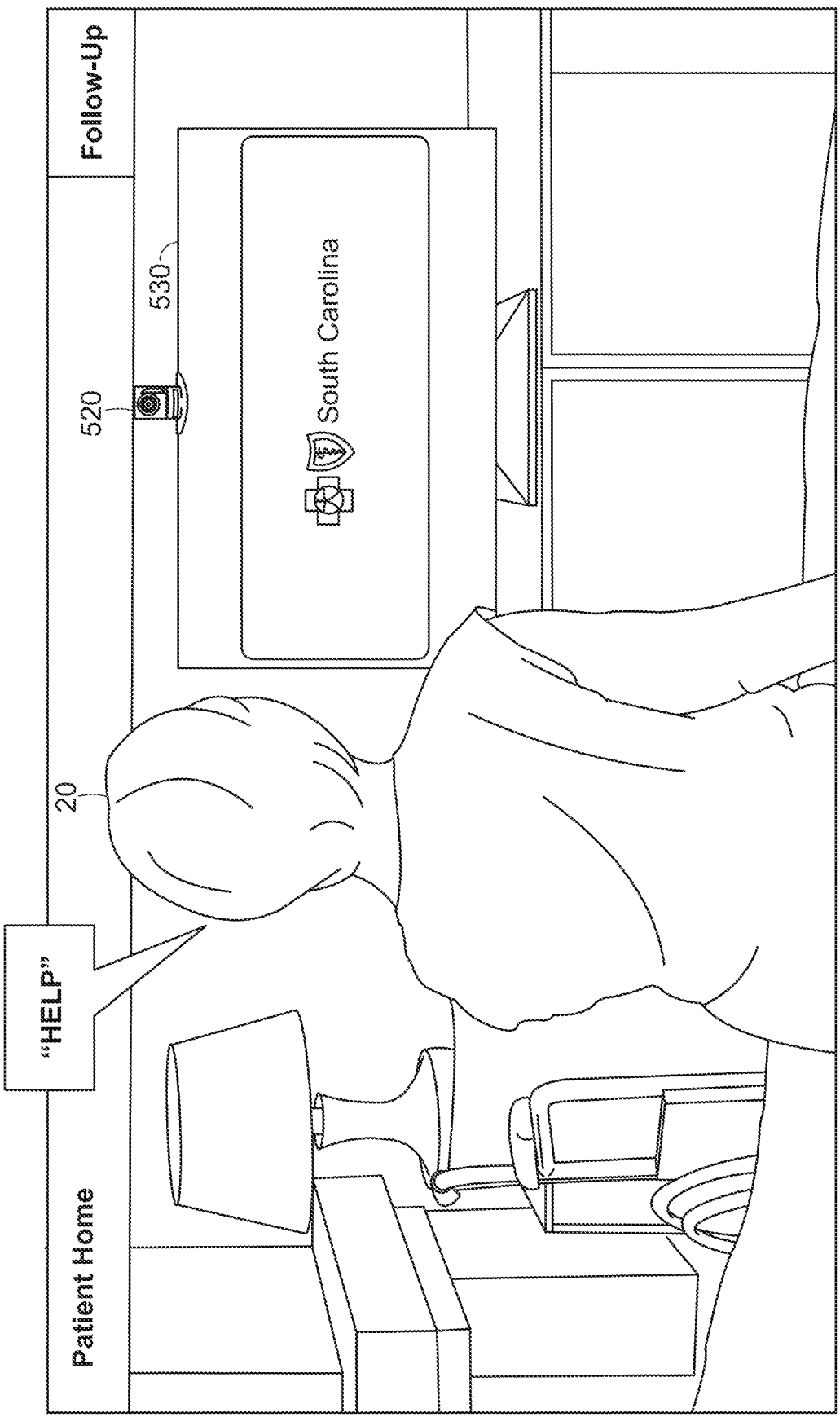
FIGS. 5A-5D depict a user using a single point device to initiate a service session with a healthcare provider.

FIGS. 5A-5D depict a user (customer) 20 using a single point device 520 to initiate a service session with a healthcare provider 30. The single point device 520 can be the single point devices 220,320,420 discussed previously with reference to FIGS. 1 and 3-4. As shown in FIG. 5A, the user 20 is watching a television program on their home display device 530. The user 20 says the words "HELP", which is captured by the single point device 520, causing the single point device 520 to activate. In response to capturing the user's 20 words ("HELP"), the single point device 520 communicates with a computerized system (such as the computerized system discussed previously with reference to FIGS. 1-2) to indicate the user 20 wishes to speak with a healthcare provider.

Figure 5B:
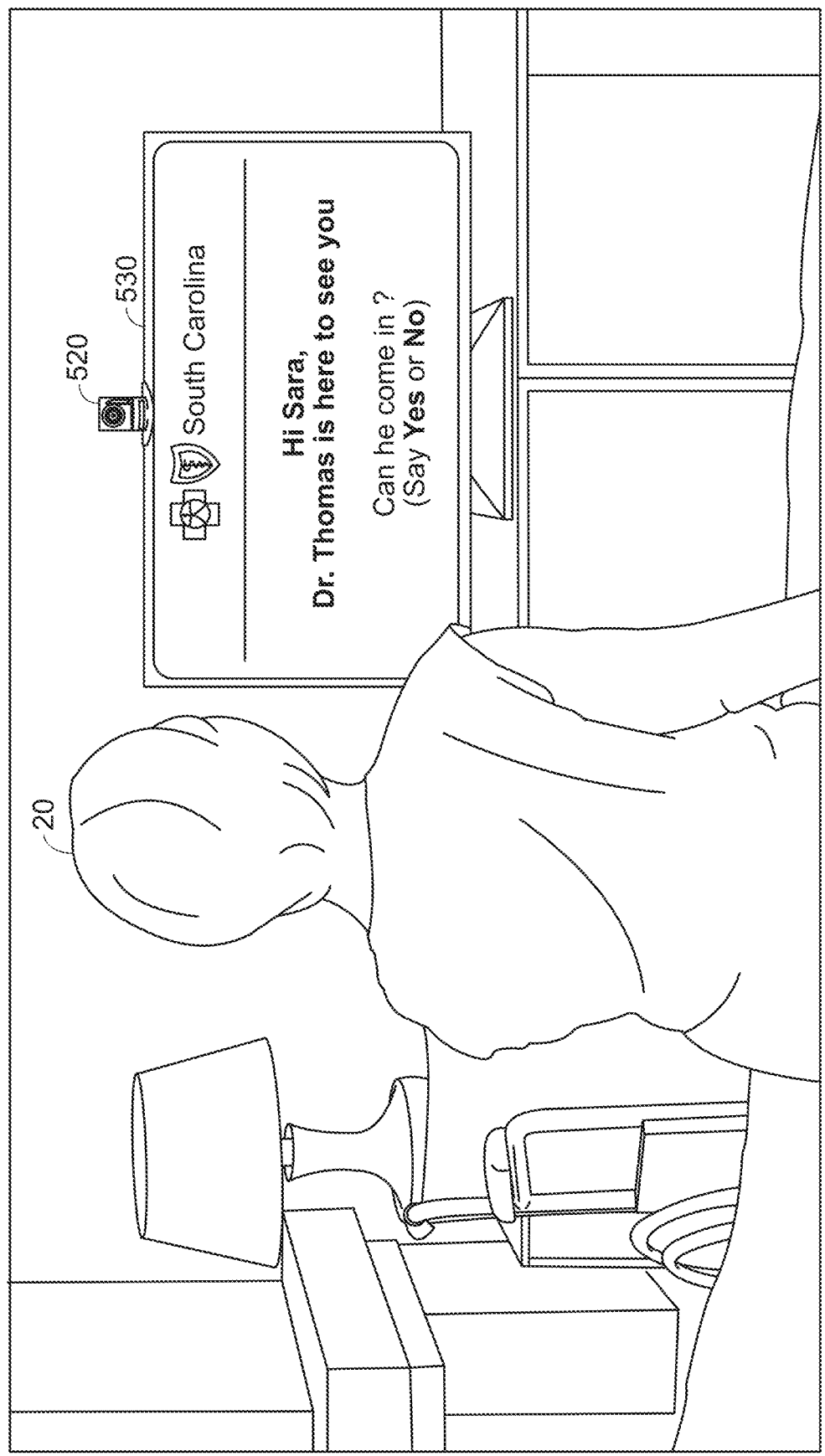

As shown in FIG. 5B, the computerized system identifies a healthcare provider 30 that is available to participate in a communication session (service session) with the user 20. The computerized system communicates with the single point device 520 that the healthcare provider is available, and the single point device 520 causes a user interface to display on the user's 20 home display device 530. As shown, the user interface fully interrupts the television program that the user 20 was watching. However, in some implementations, the user interface is displayed using picture-in-picture such that the message only partially interrupts the television program that the user 20 was watching. That is, the user interface can be displayed on one portion of the screen on the home display device 530, while the television program can continue to be displayed on another portion of the screen. In the shown implementation, the user interface includes a message that prompts the user 20 to indicate whether or not they are ready to initiate the service session with the healthcare provider 30. However, in some implementations, the message does not prompt the user 20 to indicate that they are ready, and instead informs the user that the service session is beginning (or will begin in [x] amount of time).

Figure 5C:
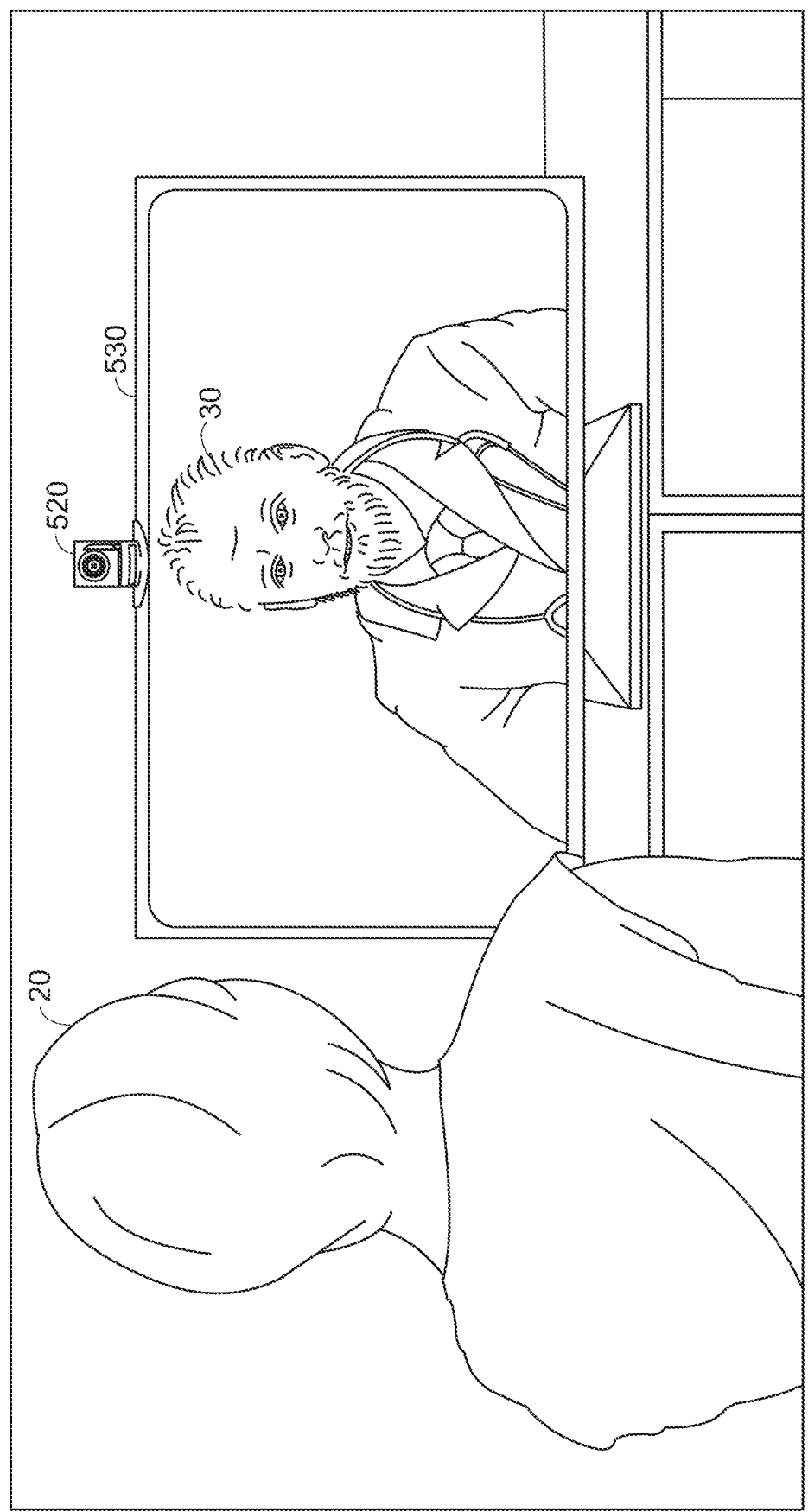

As shown in FIG. 5C, the user 20 is participating in a service session with the identified healthcare provider 30 using the single point device 520 and the home display device 530. Audio and video signals are transmitted from the web server to the single point device 520, which then causes the home display device 530 to display a video conference call in accordance with the received signals. The single point device 520 can also capture video and audio information of the user 20 and transmit this information to the web server, which then transmits this information to a device being used by the healthcare provider 30. As indicated above, although the shown embodiment shows the video conference call fully occupying the screen of the home display device 430, in some implementations, the video conference call is displayed on one portion of the screen of home display device 530, while another portion of the screen may display, for instance, the television program that the user 20 was watching prior to the video conference call.

Figure 5D:
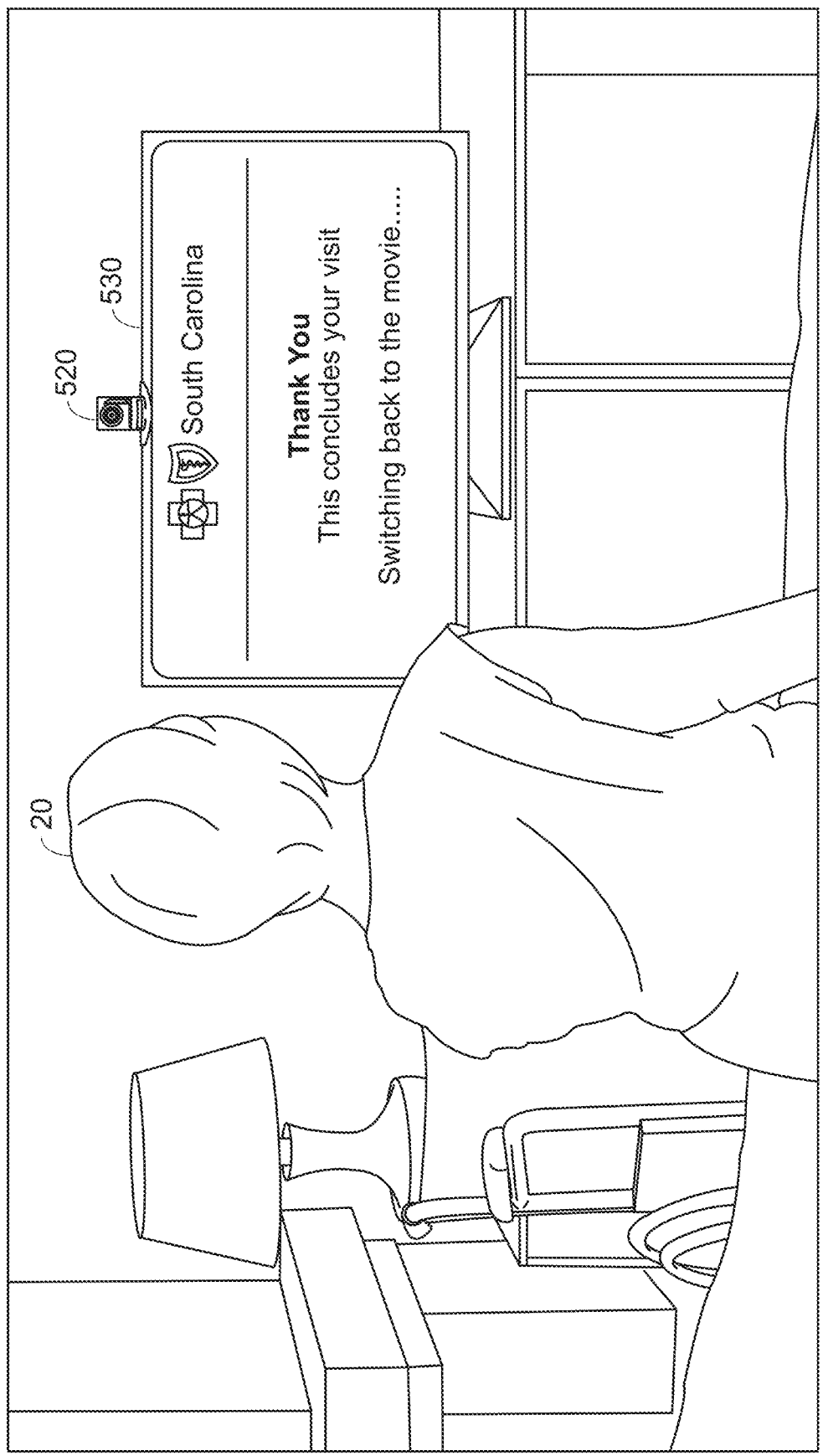

As shown in FIG. 5D, once the service session between the healthcare provider 30 and the user 20 is terminated, a message is displayed indicated that the session has been terminated and the user 20 can resume watching the television program.

Figure 5E:
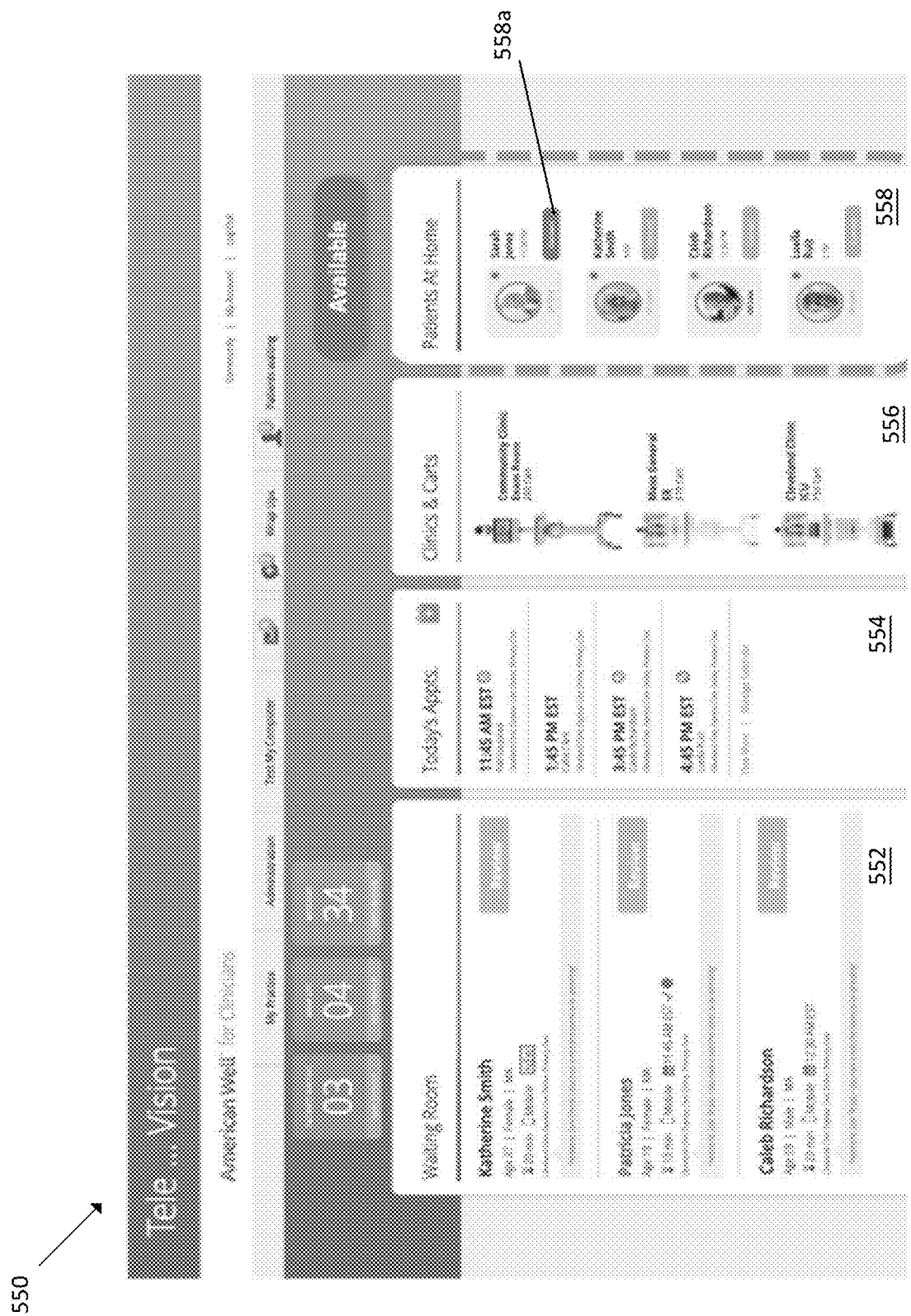
FIG. 5E depicts a provider interface that enables a provider to identify patients that are online and control communication sessions.

Referring to FIG. 5E, provider interface 550 is shown. Provider interface 550 is an interface in a physician system that allows physician to see who is online/green, e.g., in section 558. Other portions of provider interface 550 include portion 552, which lists those patients that are currently in a virtual waiting room, portion 554, which lists a physician's current appointments, and portion 556 which lists clinics that the provider is currently engaged with. In this example, portion 558 include selectable icon (or link 558a), selection of which enables a service provider to initiate a consultation with the patient represented by link 558a. In this example, the data processing system stores the contact information for the patient represented by link 558a and establishes the communication channel using the contact information.

Modes of Engagement

Figure 6:
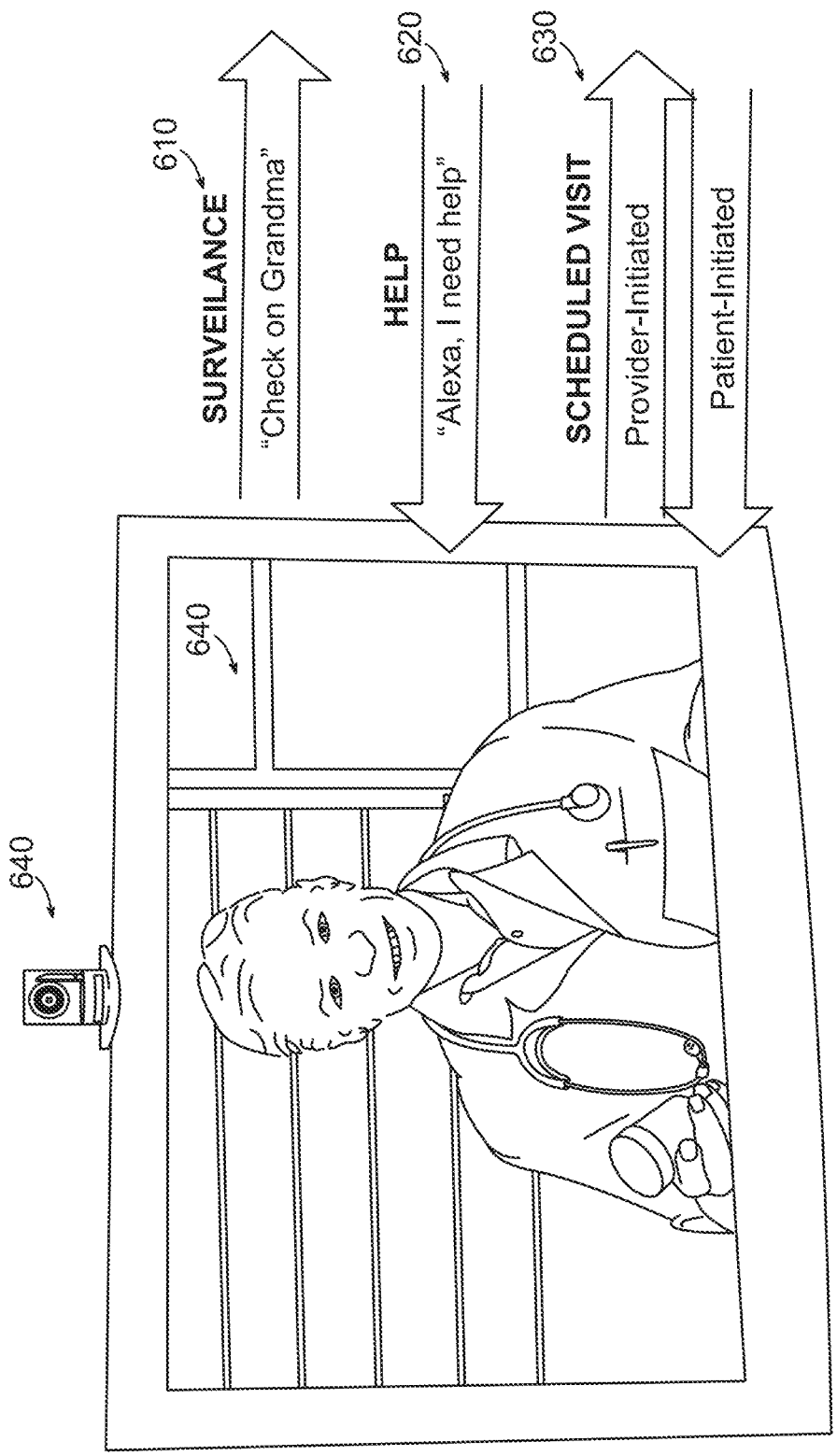
FIG. 6 illustrates several provider availability modes facilitated by a computerized system.

FIG. 6 illustrates several provider availability modes facilitated by a computerized system. Computerized systems (such as the computerized system 10 discussed previously with reference to FIG. 1) can allow consumers to engage providers (for example, health professionals) "on demand" based on one or more provider availability modes. The one or more provider availability modes include:

Surveillance 610—In surveillance mode 610, the computerized system acquires information from consumers through automated interaction (for example, rules-based interaction) in order to crystallize their needs (for example, medical risks) and better direct the consumers. The computerized system produces a surveillance plan to assess a consumer's current health status and specific medical conditions by directing the customer to follow a path of questioning that dynamically tailors itself based on information retrieved from the consumer (e.g., using predefined rules). As assessments progress, the computerized system constructs engagement suggestions that the consumer can exercise. Each suggestion can represent both the question to the provider and the type of provider appropriate to answer it. Consumers may choose to simply launch such engagements or apply their own discretion as to the phrasing and the selection of the recipient provider. The computerized system can be configured to turn on a single point device of a consumer at predefined points in time to solicit a response from the consumer to verify the consumer's current health status.

Help 620—In help mode 620, the consumer-provider interaction can involve a consumer stating a medical status. This can be a declarative statement, or in the form of a question or topic. The computerized system will assess the nature of the consumer's statement and determine the type of engagement or response that is appropriate. In some implementations, the computerized system determines an appropriate response by sending a request to a selected provider (whether online or not) and determines whether the request can be answered by the selected provider at their leisure. In some implementations, the computerized system determines whether an emergency should be indicated in the request and attempts to find a provider that has immediate availability. The computerized system informs the consumer once a response has been received and can allow the consumer to redirect the question if the consumer needs more urgent response time. In some implementations, a consumer may request help and the computerized system may "beam" in a doctor. In some implementations, the consumer may request help and the single point device may ask the consumer a series of questions that are used in identifying an appropriate service provider.

Schedule visit 630—In schedule visit mode 630, the system uses a scheduler module, such as the scheduler module 116 discussed previously with reference to FIG. 2, which locates providers and establishes engagements, to enable a consumer to schedule a visit via the system to engage such provider(s) or to find other available providers, and to sequentially engage providers. The scheduled visit can be patient-initiate or provider-initiated.

Device monitoring and Biometrics (Not shown)—Operating in the device monitoring and biometrics mode can involve a consumer being pre-established with various device monitors, such as an electrocardiograph device, a blood pressure sensor, and so forth. In some implementations, the computerized system is connected to various biometric devices (for example, devices that are present in the consumer's hospital room). As such, the information collected from these devices is readily available through the computerized system and, therefore, readily available to a physician for the service session engagement.

The use of broadband network connections can allow for real-time voice transmission over a network (such as the Internet) in what is referred to as full duplex communications (that is, both voice channels are open at the same time). Consumers can opt to have a voice conversation with their selected providers using, for example, the single point devices microphone and the speakers on their home display device. Web-based teleconferencing may use voice over internet protocol (VoIP), session initiation protocol (SIP), and so forth.

Video conferencing 640—The computerized system, through the single point device and the home display device of a consumer, supports video conferencing. This can allow consumers to, among other things, exhibit physical findings to providers. Consumers and providers may also simply prefer face-to-face communication, even if remote. Small digital cameras, referred to as webcams, attached to or integrated with the single point device can be used for video conferencing and standard software or custom software provided by the brokerage can be used. Alternatively, dedicated video conferencing communication equipment or telephones with built-in video capabilities can be used.

Semi synchronous correspondence (Not shown)—Some service session engagements of a consumer with a provider include both synchronous and asynchronous interactions. Part of the service session engagement takes place by immediate messaging between the two, but the provider may ask the consumer to take occasional asynchronous assessments if, for example, a generic line of question is desired. This can allow the provider to conduct more than one consumer service session engagement at a time while each consumer is constantly engaged. For example, semi-synchronous correspondence includes a combination of e-mail, instant messaging, test messaging, voice calls and mail messaging, and VoIP calls and VoIP messaging.

Figure 7:
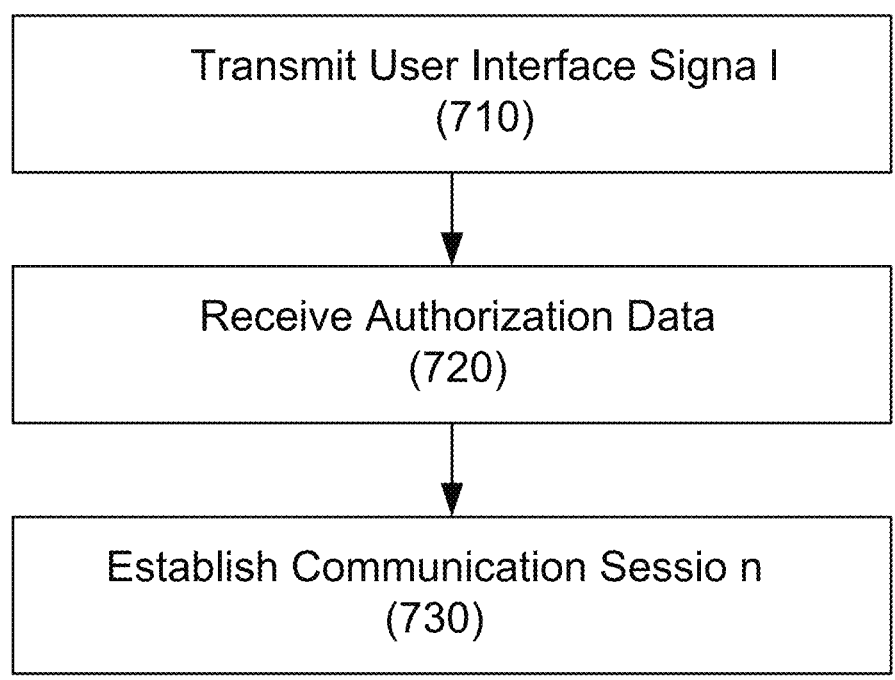
FIG. 7 is a flowchart depicting a method for rendering live streamed data.

FIG. 7 is a flowchart depicting a method 700 for rendering live streamed data. In some implementations, the method 700 is performed by the computerized system 10 discussed previously with reference to FIGS. 1-2. The method 700 includes transmitting a user interface signal (block 710), receiving authorization data (block 720), and establishing a communication session (block 730).

At block 710, a data processing system, such as the computerized system 10 discussed previously with reference to FIGS. 1-2, transmits a user interface signal to a single point device, such as the single point device 220 discussed previously with reference to FIG. 1. The user interface signal carries graphical user interface data corresponding to a graphical user interface that is capable of being rendered on a home display device, such as the home display device 230 discussed previously with reference to FIG. 1. When the home display device renders the graphical user interface, the display device interrupts displaying of a program on the display device to render the graphical user interface. The graphical user interface prompts the user (consumer) of the display device for authorization to establish a communication session through the data processing system with a client device of a medical service provider.

In some implementations, before transmitting the user interface signal, the data processing system tracks the availability of a plurality of service providers and receives, based on the tracking, an indication that one or more service providers of the plurality of service providers are available for establishing a communication session. In some implementations, two or more service providers indicate that they are available for establishing a communication session. In such instances, the computerized system can select one of the two or more service providers for establishing the communication session. The selection can be based on health data of the user of the single point device. In some implementations, the user can indicate, through the single point device, a type of medical condition the user would like to discuss (for example, kidney issues) and the computerized system can select a medical service provider most qualified to discuss kidney issues (for example, a kidney specialist).

At block 720, the data processing system receives, from the single point device, authorization data instructing the data processing system to establish the communication session. In some implementations, the communication session is a full duplex communication session. In some implementations, the communication session is a videoconference communication session.

At block 730, a communication session is established between the display device and the client device.

Embodiments can be implemented in digital electronic circuitry, or in computer hardware, firmware, software, or in combinations thereof. Apparatus of the invention can be implemented in a computer program product tangibly embodied or stored in a machine-readable storage device for execution by a programmable processor; and method actions can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired; and in any case, the language can be a compiled or interpreted language.

Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD ROM disks. Any of the foregoing can be supplemented by, or incorporated in, ASICs (application-specific integrated circuits).

Other implementations are within the scope and spirit of the description claims. For example, due to the nature of software, functions described above can be implemented using software, hardware, firmware, hardwiring, or combinations of any of these. Features implementing functions may also be physically located at various positions, including being distributed such that portions of functions are implemented at different physical locations.

What is claimed is:

1. A device, comprising:
   a display device configured to render a program and further configured to stream data for a communication session received from a data processing system, wherein the data processing system is configured to receive requests from medical service providers to initiate communication sessions with a user of the display device;
   a device configured to:
   capture image data representing at least one physical entity in a field of view of the device, and further configured to capture acoustic data, motion data, or both acoustic and motion data;
   detect an event associated with the motion data or the acoustic data;
   based on the motion data or the acoustic data, determine a health status of a patient associated with the device;
   based on the health status that is determined, determine a type of a medical service that is responsive to a health requirement of the user;
   based on the type of the medical service that is responsive, authorize establishment of a communication session with a medical service provider that provides the type of the medical service;
   based on authorizing the communication session, transmit data requesting establishment of the communication session with the medical service provider;
   based on authorizing the communication session, cause the display device to interrupt a program displayed on the display device to initiate the communication session; and
   transmit, through the data processing system and to a client device of the medical service provider, image data and additional acoustic data captured by the device.

2. The device of claim 1, wherein the device comprises a microphone.

3. The device of claim 1, wherein the device comprises a speaker device configured to output signals based on the additional acoustic data received.

4. The device of claim 1, wherein the display device comprises a television display.

5. The device of claim 1, wherein the device comprises a camera.

6. The device of claim 1, wherein causing the display device to interrupt the program comprises rendering a graphical user interface and causing display device to cease displaying of the program.

7. The device of claim 1, wherein causing the display device to interrupt the program comprises causing the display device to display a graphical user interface in a first portion of the display device and continue displaying the program in a second portion of the display device.

8. The device of claim 7, wherein the first portion is larger than the second portion.

9. The device of claim 1, wherein the communication session with the data processing system is established through a wireless network.

10. The device of claim 1, further comprising one or more biometric sensors, detecting the event comprises sensing comprise biometric data representing the health status of the patient, the biometric data representing a blood pressure, a heart status, or at least a portion of an electrocardiograph.

11. The device of claim 1, further comprising one or more motion sensors, wherein detecting the event comprises sensing motion data representing motion of a user of the device.

12. A method, comprising:
   rendering a program to stream data for a communication session received from a data processing system, wherein the data processing system is configured to receive requests from medical service providers to initiate communication sessions with a user of a display device;
   capturing image data representing at least one physical entity in a field of view of a device, and further configured to capture acoustic data, motion data, or both acoustic and motion data;
   detecting an event associated with the motion data or the acoustic data;
   based on the motion data or the acoustic data, determining a health status of a patient associated with the display device;
   based on the health status that is determined, determining a type of a medical service that is responsive to a health requirement of the user;
   based on the type of the medical service that is responsive, authorizing establishment of a communication session with a medical service provider that provides the type of the medical service;
   based on authorizing the communication session, transmitting data requesting establishment of the communication session with the medical service provider;
   based on authorizing the communication session, causing the display device to interrupt a program displayed on the display device to initiate the communication session; and transmitting, through the data processing system and to a client device of the medical service provider, image data and additional acoustic data captured by the device.

13. The method of claim 12, wherein causing the display device to interrupt the program comprises rendering a graphical user interface and causing display device to cease displaying of the program.

14. The method of claim 12, wherein causing the display device to interrupt the program comprises causing the display device to display a graphical user interface in a first portion of the display device and continue displaying the program in a second portion of the display device.

15. The method of claim 14, wherein the first portion is larger than the second portion.

* * * * *